United States Patent
Borini et al.

(10) Patent No.: US 9,989,488 B2
(45) Date of Patent: Jun. 5, 2018

(54) FIELD-EFFECT SENSOR AND ASSOCIATED METHODS

(71) Applicant: Nokia Technologies Oy, Espoo (FI)

(72) Inventors: Stefano Borini, Cambridge (GB); Richard White, Huntingdon (GB)

(73) Assignee: Nokia Technologies Oy, Espoo (FI)

(*) Notice: Subject to any disclaimer, the term of this patent is extended or adjusted under 35 U.S.C. 154(b) by 0 days. days.

(21) Appl. No.: 15/116,056

(22) PCT Filed: Feb. 9, 2015

(86) PCT No.: PCT/FI2015/050078
§ 371 (c)(1),
(2) Date: Aug. 2, 2016

(87) PCT Pub. No.: WO2015/121534
PCT Pub. Date: Aug. 20, 2015

(65) Prior Publication Data
US 2017/0176380 A1 Jun. 22, 2017

(30) Foreign Application Priority Data
Feb. 17, 2014 (GB) .................................. 1402772.6

(51) Int. Cl.
*G01N 27/414* (2006.01)
(52) U.S. Cl.
CPC ..... *G01N 27/4146* (2013.01); *G01N 27/4148* (2013.01)
(58) Field of Classification Search
CPC ........................ G01N 27/4146; G01N 27/4148
See application file for complete search history.

(56) References Cited

U.S. PATENT DOCUMENTS

| 5,719,033 A | 2/1998 | Ackley et al. |
| 9,080,928 B2 | 7/2015 | Borini et al. |

(Continued)

FOREIGN PATENT DOCUMENTS

| CN | 101048656 A | 10/2007 |
| CN | 103680994 A | 3/2014 |

(Continued)

OTHER PUBLICATIONS

Non-Final Office action received for corresponding U.S. Appl. No. 14/905,384, dated Jun. 9, 2017, 13 pages.

(Continued)

*Primary Examiner* — Long Pham
(74) *Attorney, Agent, or Firm* — Harrington & Smith

(57) ABSTRACT

An apparatus comprising: a first layer (512) configured to enable a flow of charge carriers from a source electrode (505) to a drain electrode (506); a second layer (513) configured to generate a voltage in response to a physical stimulus, the second layer (513) positioned so that the generated voltage can affect the conductance of the first layer (512); and a third layer (514) positioned between the first (512) and second (513) layers to prevent a flow of charge carriers therebetween. The third layer (514) comprises a material configured to form electric double-layers (516, 517) at the interfaces with the first (512) and second (513) layers in response to the generated voltage. The formation of the electric double-layers (516, 517) enhances the effect of the generated voltage on the conductance of the first layer (512) such that determination of the conductance of the first layer (512) can be used to allow the magnitude of the physical stimulus to be derived.

20 Claims, 8 Drawing Sheets

(56) References Cited

U.S. PATENT DOCUMENTS

| | | | |
|---|---|---|---|
| 9,318,591 | B2 | 4/2016 | Geim et al. |
| 9,618,474 | B2 | 4/2017 | Van Rooyen et al. |
| 2002/0195644 | A1 | 12/2002 | Dodabalapur et al. |
| 2004/0001778 | A1* | 1/2004 | Chen ................. B82Y 10/00 422/88 |
| 2008/0191200 | A1* | 8/2008 | Frisbie ............... C08F 293/00 257/40 |
| 2010/0032661 | A1 | 2/2010 | Osterbacka et al. |
| 2010/0112719 | A1 | 5/2010 | Doron et al. |
| 2011/0057168 | A1 | 3/2011 | Kobayashi |
| 2011/0101309 | A1 | 5/2011 | Lin et al. |
| 2012/0049160 | A1 | 3/2012 | Sano et al. |
| 2012/0058350 | A1 | 3/2012 | Long et al. |
| 2013/0018599 | A1 | 1/2013 | Peng |
| 2013/0037780 | A1 | 2/2013 | Kivioja et al. |
| 2013/0099211 | A1 | 4/2013 | Katz et al. |
| 2013/0203198 | A1 | 8/2013 | Min et al. |
| 2013/0313522 | A1 | 11/2013 | Nourbakhsh et al. |
| 2014/0061590 | A1* | 3/2014 | Lee .................... H01L 29/1606 257/29 |
| 2014/0349211 | A1 | 11/2014 | Wei et al. |

FOREIGN PATENT DOCUMENTS

| | | |
|---|---|---|
| EP | 1786049 A1 | 5/2007 |
| EP | 2108198 A1 | 10/2009 |
| EP | 2629356 A1 | 8/2013 |
| JP | S52-070884 A | 6/1977 |
| JP | S61-149857 A | 7/1986 |
| JP | S61-173148 A | 8/1986 |
| JP | H04-361149 A | 12/1992 |
| JP | H09-218172 A | 8/1997 |
| JP | 2005-533371 A | 11/2005 |
| JP | 2012-247189 A | 12/2012 |
| WO | 2008/090257 A1 | 7/2008 |
| WO | 2012/033869 A1 | 3/2012 |
| WO | 2012/043912 A1 | 4/2012 |
| WO | 2012/114208 A1 | 8/2012 |
| WO | 2013/105449 A1 | 7/2013 |

OTHER PUBLICATIONS

Extended European Search Report received for corresponding European Patent Application No. 15748554.1, dated Jul. 26, 2017, 19 pages.

Klug et al., "Organic Field-Effect Transistor Based Sensors with Sensitive Gate Dielectrics Used for Low-Concentration Ammonia Detection", Organic Electronics, vol. 14, No. 2, Feb. 2013, pp. 500-504.

Fabiano et al., "Ferroelectric Polarization Induces Electric Double Layer Bistability in Electrolyte-Gated Field-Effect Transistors", ACS Appl. Mater. Interfaces, 6 (1), 2014, pp. 438-442.

Lee et al., "Ion Gel Gated Polymer Thin-Film Transistors", Journal of the American Chemical Society, vol. 129, 2007, pp. 4532-4533.

Kim et al., "Large-Scale Graphene Micropatterns via Self-Assembly-Mediated Process for Flexible Device Application", Nano Letters, vol. 12, No. 2, 2012, pp. 743-748.

Liao et al., "Highly Selective and Sensitive Glucose Sensors Based on Organic Electrochemical Transistors with Graphene-Modified Gate Electrodes", Journal of Materials Chemistry B, 2013, 1, No. 31, pp. 3820-3829.

Maiolo et al., "Flexible PVDF-TrFE Pyroelectric Sensor Integrated on a Fully Printed P-channel Organic Transistor", Procedia Engineering, vol. 47, 2012, pp. 526-529.

Dahiya et al., "Piezoelectric Oxide Semiconductor Field Effect Transistor Touch Sensing Devices", Applied Physics Letters, vol. 95, No. 3, 2009, pp. 1-3.

Office action received for corresponding Japanese Patent Application No. 2016-552279, dated Jul. 27, 2017, 4 pages of office action and 5 pages of translation available.

Schedin et al., "Detection of Individual Gas Molecules adsorbed on Graphene", Nature Materials, vol. 6, Sep. 2007, pp. 652-655.

Yao et al., "Electric Current Induced Reduction of Graphene Oxide and Its Application as Gap Electrodes in Organic photoswitching Devices", Advance Materials, 2010, pp. 5008-5012.

Nair et al., "Unimpeded Permeation of WaterThrough Helium-leak-Tight Graphene-Based Membranes", Science , vol. 335, Jan. 27, 2012, pp. 442-444.

Dimiev et al., "Graphene Oxide. Origin of Acidity, Its Instability in Water, and a New Dynamic Structural Model", ACSNano , vol. 7, No. 1, 2013, pp. 576-588.

"Graphene Oxide", Graphene square, Retrieved on Mar. 6, 2017, Webpage available at : http://www.graphenesq.com/products/product_detail.asp?idx=51&p_cate1=630&smenu=3.

Yao et al., "The Effect of Ambient Humidity on the Electrical Properties of Graphene Oxide Films", Nanoscale Research Letters, 2012, pp. 1-7.

Zhao et al., "Humidity Sensing Properties of the Sensor Based on Graphene Oxide Films With Different Dispersion Concentrations", IEEE Sensors, Oct. 28-31, 2011, 4 Pages.

"Graphene the Wonder woman", Science Articles & Inventions Online, Retrieved on Mar. 6, 2017, Webpage available at : http://sciencearticlesonline.com/2012/01/30/is-graphene-the-material-of-the-century-what-cant-it-do-see-here/.

Lee et al., "Cut and stick" rubbery ion gels as high capacitance gate dielectrics, Adv Mater, vol. 24, Issue 32, Aug. 22, 2012, pp. 4457-4462.

Sagar et al., "Polymer-electrolyte Gated Graphene Transistors for Analog and Digital Phase Detection", Applied physics Letters, vol. 99, No. 4, 2011, 4 pages.

Vasu et al., "Probing Top-gated Field Effect Transistor of Reduced Graphene Oxide Monolayer Made by Dielectrophoresis", Solid State Communications, vol. 150, No. 29-30, Aug. 2010, pp. 1-12.

Sagar, "Graphene-based Field-effect Transistors", Thesis, 2011, 113 pages.

Chakraborty et al., "The Formation of a P-n Junction in a Polymer Electrolyte Top-gated Bilayer Graphene Transistor", Nanotechnology, Sep. 5, 2009, 16 pages.

Sharma et al., "Graphene Based Field Effect Transistors: Efforts Made Towards Flexible Electronics", Solid-State Electronics, Nov. 2013, pp. 177-188.

Search Report received for corresponding United Kingdom Patent Application No. 1402772.6, dated Aug. 14, 2014, 3 pages.

International Search Report and Written Opinion received for corresponding Patent Cooperation Treaty Application No. PCT/FI2015/050078, dated May 8, 2015, 16 pages.

* cited by examiner

Figure 1b  T=25°C

FIELD-EFFECT SENSOR AND ASSOCIATED METHODS

RELATED APPLICATION

This application was originally filed as PCT Application No. PCT/FI2015/050078 filed Feb. 9, 2015, which claims priority benefit from GB Patent Application No. 1402772.6, filed Feb. 17, 2014.

TECHNICAL FIELD

The present disclosure relates to the field of environmental sensors, associated methods and apparatus, and in particular concerns an apparatus for use in determining the presence and/or magnitude of a physical stimulus based on the conductance of a material layer. Certain disclosed example aspects/embodiments relate to portable electronic devices, in particular, so-called hand-portable electronic devices which may be hand-held in use (although they may be placed in a cradle in use). Such hand-portable electronic devices include so-called Personal Digital Assistants (PDAs) and tablet PCs.

The portable electronic devices/apparatus according to one or more disclosed example aspects/embodiments may provide one or more audio/text/video communication functions (e.g. tele-communication, video-communication, and/or text transmission, Short Message Service (SMS)/Multimedia Message Service (MMS)/emailing functions, interactive/non-interactive viewing functions (e.g. web-browsing, navigation, TV/program viewing functions), music recording/playing functions (e.g. MP3 or other format and/or (FM/AM) radio broadcast recording/playing), downloading/sending of data functions, image capture function (e.g. using a (e.g. in-built) digital camera), and gaming functions.

BACKGROUND

Research is currently being done to develop new sensors (such as environmental sensors) which can be produced at lower cost with improved sensitivity when compared to existing sensors.

One or more aspects/embodiments of the present disclosure may or may not address one or more of these issues.

The listing or discussion of a prior-published document or any background in this specification should not necessarily be taken as an acknowledgement that the document or background is part of the state of the art or is common general knowledge.

SUMMARY

According to a first aspect, there is provided an apparatus comprising:
- a first layer configured to enable a flow of charge carriers from a source electrode to a drain electrode;
- a second layer configured to generate a voltage in response to a physical stimulus which is proportional to the magnitude of the physical stimulus, the second layer positioned such that the generated voltage can affect the conductance of the first layer; and
- a third layer positioned between the first and second layers to prevent a flow of charge carriers therebetween,
wherein the third layer comprises a material configured to form electric double-layers at the interfaces with the first and second layers in response to the generated voltage, formation of the electric double-layers enhancing the effect of the generated voltage on the conductance of the first layer such that determination of the conductance of the first layer can be used to allow the presence and/or magnitude of the physical stimulus to be derived.

The physical stimulus may be a chemical or biological species. The second layer may be configured to generate a voltage which is proportional to the amount of chemical or biological species to which the second layer is exposed. The chemical species may be water. The second layer may comprise a junction of graphene oxide and reduced graphene oxide. The second layer may comprise a junction of first and second materials each having one or more functional groups configured to release charged particles on interaction with the chemical or biological species. The first material may have a higher concentration of charge-releasing functional groups than the second material such that a concentration gradient of charged particles is produced at the junction on exposure to the chemical or biological species to generate the voltage. The chemical species may be water. The first and second materials may comprise graphene oxide and reduced graphene oxide, respectively. The charged particles may be protons. The charge-releasing functional groups may comprise one or more of carboxyl, hydroxyl and epoxy groups.

The physical stimulus may be heat. The second layer may comprise a pyroelectric material configured to generate a voltage which is proportional to the temperature of the pyroelectric material. The pyroelectric material may comprise one or more of polyvinylidene fluoride, P(VDF-trifluoroethylene), lithium tantalate and gallium nitride.

The physical stimulus may be electromagnetic radiation. The electromagnetic radiation may comprise one or more of visible, infrared and UV light. The second layer may comprise a photovoltaic cell configured to generate a voltage which is proportional to the intensity of electromagnetic radiation incident upon the photovoltaic cell. The photovoltaic cell may comprise a layer of polyacetylene positioned between an indium tin oxide electrode and an aluminium electrode.

The physical stimulus may be mechanical stress. The mechanical stress may comprise one or more of compressive, tensile and shearing stress. The second layer may comprise a piezoelectric material configured to generate a voltage which is proportional to the magnitude of stress applied to the piezoelectric material. The piezoelectric material may comprise one or more of polyvinylidene fluoride, lead zirconium titanate, barium titanate and zinc oxide.

The physical stimulus may be an electric field. The second layer may comprise a ferroelectric material configured to generate a voltage which is proportional to the strength of electric field to which the ferroelectric material is exposed. The ferroelectric material may comprise one or more of polyvinylidene fluoride, barium titanate and lead titanate.

The apparatus/second layer may be configured to detect/sense one or more of the above-mentioned physical stimuli.

The apparatus may have a substantially planar configuration in which the second layer is adjacent to the first layer. The apparatus may have a stacked configuration in which the second layer overlies the first layer.

The first layer may have a thickness of one atomic layer. The first layer may comprise a thin-film semiconductor such as silicon or graphene. The first layer may comprise an organic semiconductor such as poly(3-hexylthiophene-2,5- diyl). The first layer may be patterned to form a channel between the source and drain electrodes.

The material of the third layer may comprise one or more of a liquid and a gel. The gel may comprise a polymeric structure in which ions are solvated and mobile. The material of the third layer may comprise one or more of an ion gel, an ionic fluid, an ionic liquid, an electrolyte, a solid electrolyte, a gel electrolyte and a polymer electrolyte. The polymer electrolyte may comprise poly(vinylidene fluoride-co-hexafluoropropylene) and 1-ethyl-3-methylimidazolium bis(trifluoromethylsulfonyl)amide, or poly(ethylene oxide) and lithium perchlorate. The liquid or gel may be contained within another material to restrict the flow of the liquid or gel.

The apparatus may comprise a protective layer configured to prevent damage to at least the second layer without preventing exposure of the second layer to the physical stimulus.

The apparatus may comprise the source and drain electrodes. The apparatus may comprise a gate electrode positioned between the second and third layers. The apparatus may comprise means for determining the conductance of the first layer. The apparatus may comprise means for deriving the magnitude of the physical stimulus using a determination of the conductance of the first layer.

The physical stimulus may be water. Determination of the conductance of the first layer may be used to provide an indication of the relative humidity of the environment in which the apparatus is located.

The apparatus may be one or more of an electronic device, a portable electronic device, a portable telecommunications device, a sensor and a module for any of the aforementioned devices.

According to a further aspect, there is provided a method of using an apparatus, the apparatus comprising:
  a first layer configured to enable a flow of charge carriers from a source electrode to a drain electrode;
  a second layer configured to generate a voltage in response to a physical stimulus which is proportional to the magnitude of the physical stimulus, the second layer positioned such that the generated voltage can affect the conductance of the first layer; and
  a third layer positioned between the first and second layers to prevent a flow of charge carriers therebetween,
  wherein the third layer comprises a material configured to form electric double-layers at the interfaces with the first and second layers in response to the generated voltage, formation of the electric double-layers enhancing the effect of the generated voltage on the conductance of the first layer such that determination of the conductance of the first layer can be used to allow the presence and/or magnitude of the physical stimulus to be derived, the method comprising:
  determining the conductance of the first layer; and
  deriving the presence and/or magnitude of the physical stimulus using the determined conductance of the first layer.

According to a further aspect, there is provided a method of making an apparatus, the method comprising:
  forming first, second and third layers of the apparatus,
  the first layer configured to enable a flow of charge carriers from a source electrode to a drain electrode;
  the second layer configured to generate a voltage in response to a physical stimulus which is proportional to the magnitude of the physical stimulus, the second layer positioned such that the generated voltage can affect the conductance of the first layer; and
  the third layer positioned between the first and second layers to prevent a flow of charge carriers therebetween,
  wherein the third layer comprises a material configured to form electric double-layers at the interfaces with the first and second layers in response to the generated voltage, formation of the electric double-layers enhancing the effect of the generated voltage on the conductance of the first layer such that determination of the conductance of the first layer can be used to allow the presence and/or magnitude of the physical stimulus to be derived.

The steps of any method disclosed herein do not have to be performed in the exact order disclosed, unless explicitly stated or understood by the skilled person.

Corresponding computer programs (which may or may not be recorded on a carrier) for implementing one or more of the methods disclosed herein are also within the present disclosure and encompassed by one or more of the described example embodiments.

The present disclosure includes one or more corresponding aspects, example embodiments or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which:

FIG. 1b shows impedance spectra (frequency range 40 Hz-110 MHz) of graphene oxide as a function of relative humidity;

FIG. 8b shows an equivalent circuit diagram for the apparatus of FIG. 8a;

DESCRIPTION OF SPECIFIC ASPECTS/EMBODIMENTS

Figure 1A:
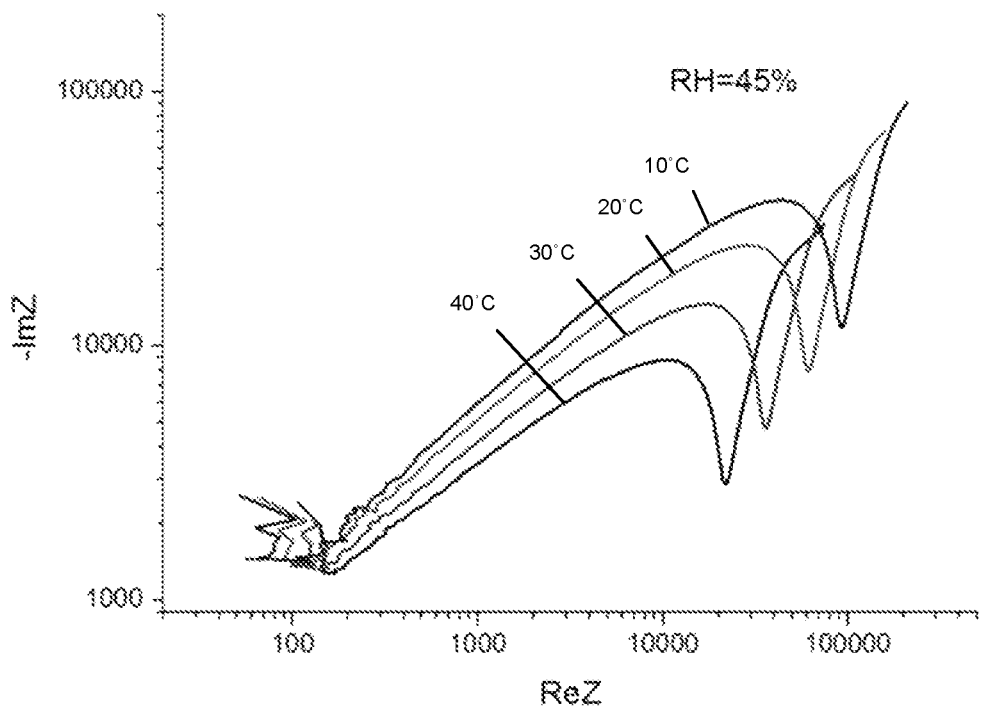
FIG. 1a shows impedance spectra (frequency range 40 Hz-110 MHz) of graphene oxide as a function of temperature.
Figure 1A:
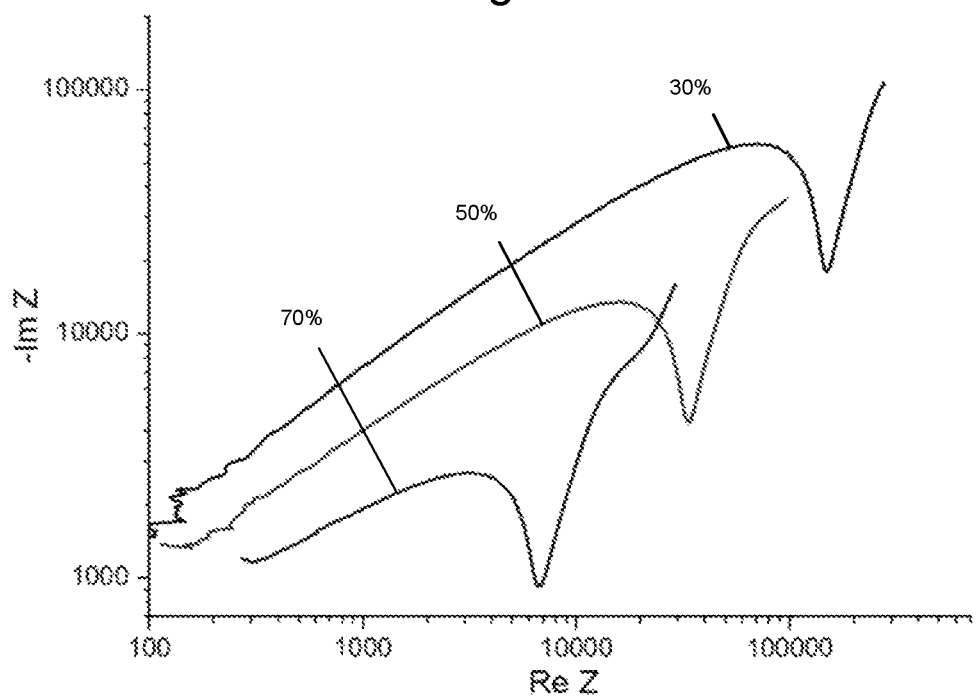

Graphene oxide has recently been considered as a novel material for use in temperature and humidity sensors. The use of graphene oxide as the sensing material enables transparent, flexible sensors to be produced at low cost with improved sensitivity when compared to existing sensors The impedance of graphene oxide has been found to be exponentially dependent upon the temperature and relative humidity of the environment in which it is located. This is illustrated in FIGS. 1a and 1b which show complex impedance spectra of graphene oxide as a function of temperature (at a relative humidity of 45%) and relative humidity (at a temperature of 25° C.), respectively.

Figure 2:
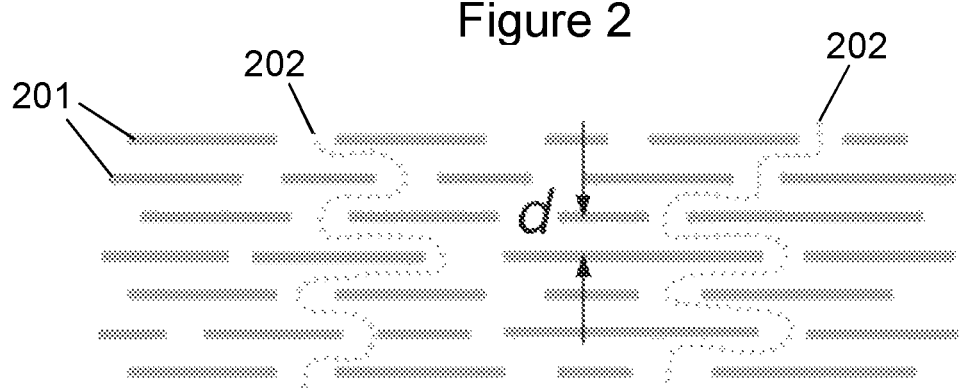
FIG. 2 shows water evaporation through a pseudo two-dimensional stack of graphene oxide platelets.

The temperature and humidity dependence is not fully understood, but may relate to the layered structure of the material. As shown in FIG. 2, graphene oxide comprises a stack of pseudo two-dimensional platelets 201 (with interstitial spacing "d") which allow the permeation of water 202 through the material. The permeation rate depends on both the temperature and relative humidity of the environment.

Figure 3:
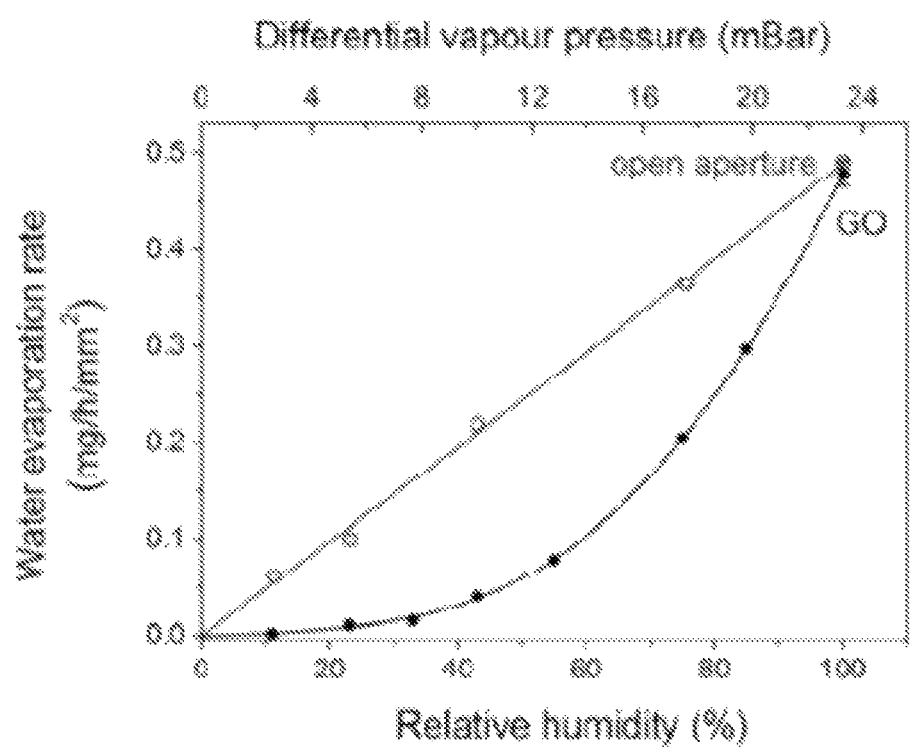
FIG. 3 shows the water permeation rate through an open aperture with and without a graphene oxide membrane as a function of relative humidity.

FIG. 3 shows the rate of water evaporation through an open aperture and the same aperture covered with a 0.5 μm thick graphene oxide membrane. At 100% relative humidity, the water penetrates through the graphene oxide as though the membrane wasn't there. One possible explanation for this behaviour is that the relative humidity (and also the temperature) of the surrounding environment affect the interstitial spacing of the graphene oxide platelets, which in turn dictates the amount of water that can be absorbed by the material. When water fills the space between the platelets, the thickness of the material increases and protons are dissociated from the graphene oxide. The protons and water molecules form a hydronium ion which is mobile within the graphene oxide-water complex resulting in the change in impedance.

Graphene oxide-based sensors, however, have been found to suffer from the following drawbacks:

(i) Structural degradation—it is known that irreversible modification of graphene oxide occurs during exposure to water (both liquid and vapour) and is thought to be accelerated when there is current flow through the graphene oxide layer.

(ii) Low conductivity—graphene oxide is an insulator and graphene oxide layers of <50 nm in thickness (required for transparency and speed) have sheet resistances of >GΩ/sq. For typical interdigitated electrode designs, especially those using printed electrodes, this constrains the footprint of the sensor to be several tens of mm². In some circumstances it may be desirable to shrink this sensor layout size.

(iii) AC operation—it has been observed that the operation of graphene oxide sensors under a DC bias results in the build up of an open circuit voltage across the graphene oxide sensing layer and instability in the DC conductance measurement. This has led to the graphene oxide sensors being measured using either AC or pulsed excitation. In some circumstances DC operation may be desirable.

(iv) Sensitivity—although graphene oxide is highly sensitive to relative humidity, a trade-off exists between sensitivity and thickness (which affects transparency and speed).

There will now be described an apparatus and associated methods that may or may not provide a solution to one or more of these issues.

Figure 4:
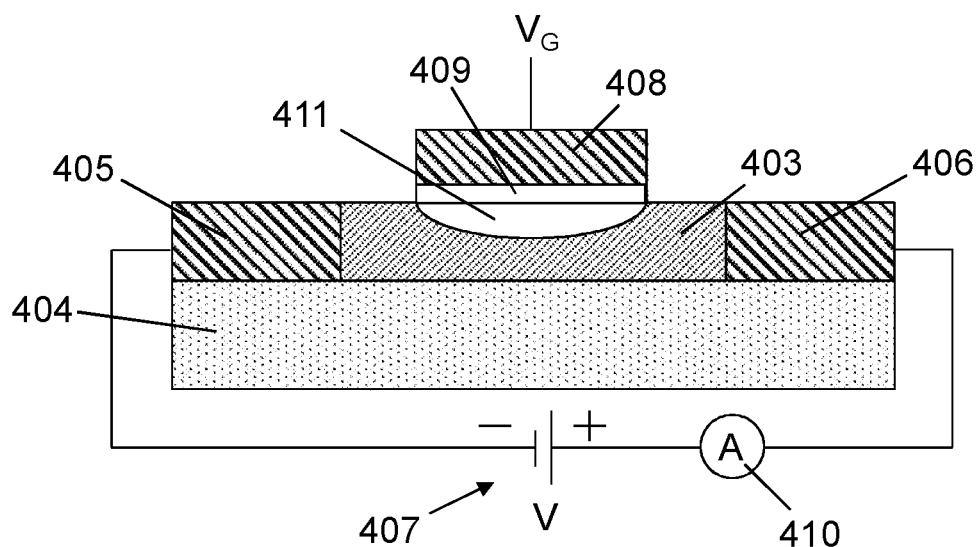
FIG. 4 shows a conventional field effect transistor (cross-section)

One or more disclosed embodiments of the present apparatus comprise a field effect transistor (FET) for use in sensing/detecting a physical stimulus in an environment in which the apparatus is located. An FET is a type of transistor in which an electrical current is carried along a conduction channel, the conductance of which can be controlled by a transverse electric field. In a conventional FET setup (as illustrated in FIG. 4 in cross-section), a semiconductor 403 such as p-type silicon is supported on a substrate 404 and connected to metal source 405 and drain 406 electrodes. A current is injected and collected via the source 405 and drain 406 electrodes, respectively, by applying a potential difference (V) 407 across the semiconductor 403. The conductance of the semiconductor 403 between the source 405 and drain 406 electrodes is switched on and off by a third electrode (the gate electrode 408) capacitively coupled through a thin dielectric layer 409. The conductance may be determined by measuring the current through the semiconductor 403 (using an ammeter 410, for example) and dividing by the potential difference (V) 407. With p-type silicon (or another p-type semiconductor), application of a positive gate voltage ($V_G$) depletes the charge carriers (creating a depletion region 411 in the semiconductor 403) and reduces the conductance, whilst applying a negative gate voltage ($V_G$) leads to an accumulation of charge carriers (creating a conductive region) and an increase in conductance.

Figure 5:
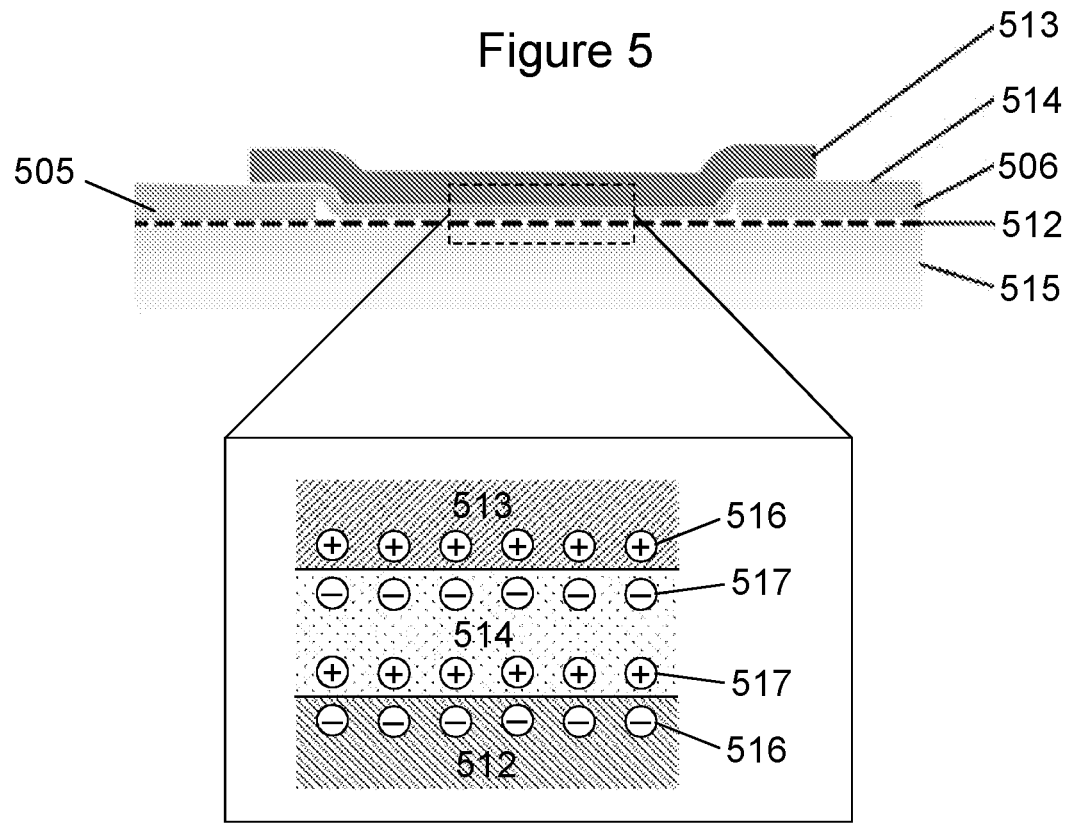
FIG. 5 shows an apparatus according to one embodiment of the present disclosure (cross-section)

As shown in cross-section in FIG. 5, one embodiment of the present apparatus comprises a first layer 512 configured to enable a flow of charge carriers from a source electrode 505 to a drain electrode 506, a second layer 513 configured to generate a voltage in response to a physical stimulus which is proportional to the magnitude of the physical stimulus, and a third layer 514 positioned between the first 512 and second 513 layers to prevent a flow of charge carriers therebetween. The first 512, second 513 and third 514 layers, and the source 505 and drain 506 electrodes may be formed on top of a supporting substrate 515.

The second layer 513 is positioned such that the generated voltage can affect the conductance of the first layer 512, and the third layer 514 comprises a material (e.g. an ion gel, ionic fluid, ionic liquid, electrolyte, solid electrolyte, gel electrolyte and/or polymer electrolyte) configured to form electric double-layers at the interfaces with the first 512 and second 513 layers in response to the generated voltage. An electric double-layer is a structure that forms at the surface of a charged object when it is in contact with a fluid. The charges 516 on the surface of the object at the object-fluid interface attract oppositely charged ions 517 in the fluid towards the surface charge 516. The ions 517 then arrange themselves at the interface to mirror the surface charge 516 and form an insulating structure. In an electric double-layer (i.e. a layer of surface charge 516 and a layer of ions 517), the separation d of the surface charge 516 and ions 517 is on the order of nanometres. This small separation results in a large capacitance at the object-fluid interface, a feature which is currently exploited in supercapacitors.

Due to the large capacitance associated with an electric double-layer, formation of these structures at the layer interfaces enhances the effect of the generated voltage on the conductance of the first layer 512. In this way, generated voltages of less than 1V can be used to influence the conductance of the first layer 512, thereby allowing the presence and/or magnitude of the physical stimulus to be derived using a determination of the conductance. This relatively high sensitivity of the first layer conductance to the generated voltage also enables the present apparatus to be switched between "on" and "off" states by the physical stimulus, thus providing a binary output if desirable.

Since the electrical current is passed through the first layer 512 rather than the second (i.e. stimulus-sensitive) layer 513 during operation, graphene oxide may be used in the second layer 513 without suffering from the above-mentioned structural degradation, low conductivity and DC instability issues. Furthermore, any reduction in sensitivity caused by the low thickness of the graphene oxide can be compensated for by using an ultrasensitive material (e.g. graphene) in the first layer 512.

Figure 6:
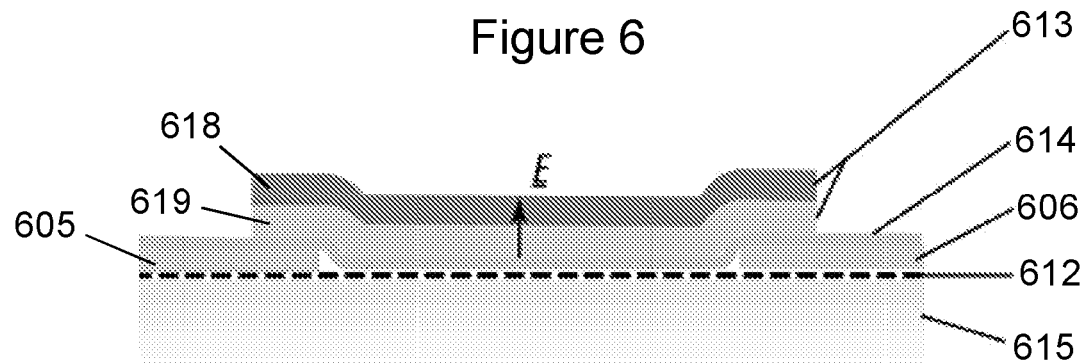
FIG. 6 shows an apparatus according to another embodiment of the present disclosure (cross-section)

The present apparatus may be used to detect/measure a number of different physical stimuli depending on the material(s) used to form the second layer 513. For example, the physical stimulus may be a chemical or biological species, and the second layer 513 may be configured to generate a voltage which is proportional to the amount of chemical or biological species to which the second layer 513 is exposed. As shown in cross-section in FIG. 6, the second layer 613 may comprise a junction of first 618 and second 619 materials each having one or more functional groups configured to release charged particles on interaction with the chemical or biological species. When the first material 618 has a higher concentration of charge-releasing functional groups than the second material 619, a concentration gradient of charged particles can be produced at the junction on exposure to the chemical or biological species to generate the voltage.

Figure 7:
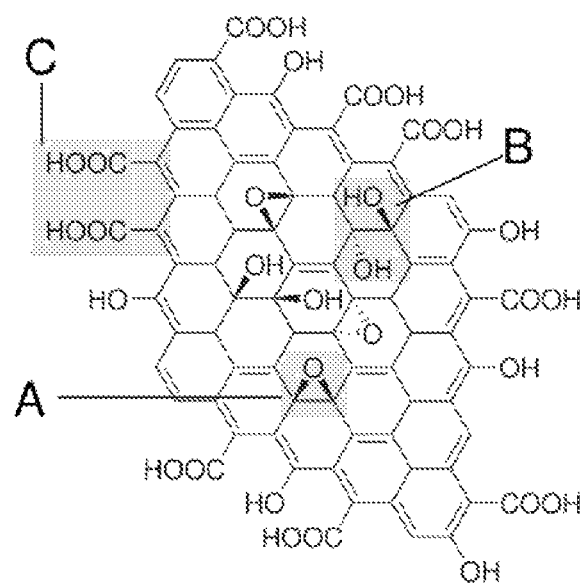
FIG. 7 shows the chemical structure of graphene oxide.

For humidity sensing, the chemical species would be water, and the first 618 and second 619 materials may comprise graphene oxide and reduced graphene oxide, respectively. Graphene oxide may be considered as graphene with one or more functional groups attached thereto, such as carboxyl (c), hydroxyl (B) and/or epoxy (A) groups as shown in FIG. 7. When such a material interacts with water, protonation occurs at the surface of the material causing the dissociation of protons ($H^+$) from the functional groups (A-C). The protons diffuse through the junction until a dynamic thermal equilibrium is reached, giving rise to a built-in potential. Different relative humidity levels create different proton gradients and therefore different characteristic open-circuit voltages at equilibrium. This concept can be extended to different surface functionalizations (i.e. to detect different chemical or biological species) using either functionalized graphene or other two-dimensional materials such as boron nitride, molybdenum disulphide, niobium diselenide, or a high temperature superconductor such as $Bi_2Sr_2CaCu_2O_x$.

The apparatus could also be used to detect heat, electromagnetic radiation, mechanical stress or an electric field. When the physical stimulus is heat, the second layer 613 may comprise a pyroelectric material (e.g. polyvinylidene fluoride, P(VDF-trifluoroethylene), lithium tantalate and gallium nitride) configured to generate a voltage which is proportional to the temperature of the pyroelectric material. When the physical stimulus is electromagnetic radiation, the second layer 613 may comprise a photovoltaic cell (e.g. comprising a layer of polyacetylene positioned between an indium tin oxide electrode and an aluminium electrode) configured to generate a voltage which is proportional to the intensity of electromagnetic radiation incident upon the photovoltaic cell. When the physical stimulus is mechanical stress, the second layer 613 may comprise a piezoelectric material (e.g. polyvinylidene fluoride, lead zirconium titanate, barium titanate and zinc oxide) configured to generate a voltage which is proportional to the magnitude of stress applied to the piezoelectric material. When the physical stimulus is an electric field, the second layer 613 may comprise a ferroelectric material (e.g. polyvinylidene fluoride, barium titanate and lead titanate) configured to generate a voltage which is proportional to the strength of electric field to which the ferroelectric material is exposed.

The sensitivity of the apparatus can be increased in several different ways. One method is to use a material in the first layer 612 whose conductance is highly sensitive to local changes in electric field strength. The sensitivity can be increased further by patterning the first layer 612 to form a channel between the source 605 and drain 606 electrodes and/or by reducing the thickness of the first layer 612. Ideally the first layer 612 should have a thickness of one atomic layer, which is achievable with two-dimensional crystal materials. In this respect, graphene is a suitable candidate for the first layer 612.

Figure 8A:
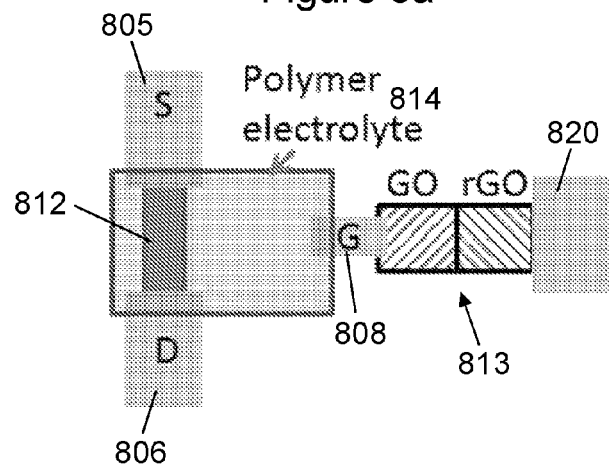
FIG. 8a shows an apparatus according to another embodiment of the present disclosure (plan view)
Figure 8B:
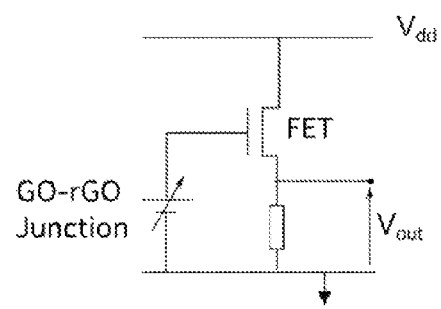

FIG. 8a shows one embodiment of the present apparatus (in plan view) which is configured to sense the relative humidity of the environment in which the apparatus is located, and FIG. 8b shows the equivalent circuit diagram. In this embodiment, the first layer 812 comprises graphene, the second layer 813 comprises a junction formed from graphene oxide and reduced graphene oxide, and the third layer 814 comprises a polymer electrolyte formed from poly(vinylidene fluoride-co-hexafluoropropylene) and 1-ethyl-3-methylimidazolium bis(trifluoromethylsulfonyl) amide. The apparatus also comprises the source 805 and drain 806 electrodes, a gate electrode 808 positioned between the second 813 and third 814 layers, and a reference electrode 820 in contact with the second layer 813. The gate electrode 808 helps to evenly distribute the surface charge produced at the surface of the second layer 813 to provide a more uniform electric double-layer with the polymer electrolyte 814, whilst the reference electrode 820 is used to ensure that the second layer 813 (and gate electrode 808) is at a different voltage (ground in FIG. 8b, but it could be $V_{dd}$) to the source 805 or drain 806 electrode.

Unlike the previously illustrated embodiments in which the second layer 813 overlies the first layer 812 (i.e. a stacked configuration), this embodiment comprises a substantially planar configuration in which the second layer 813 is adjacent to the first layer 812. This "offset" gate structure is possible due to the use of a fluidic third layer 814 instead of a conventional dielectric. This is because the insulating electric double-layers are produced at the layer interfaces regardless of the relative positions of the first 812 and second 813 layers. The planar configuration simplifies the fabrication process and is also less prone to short-circuits than the stacked configuration.

Figure 9A:
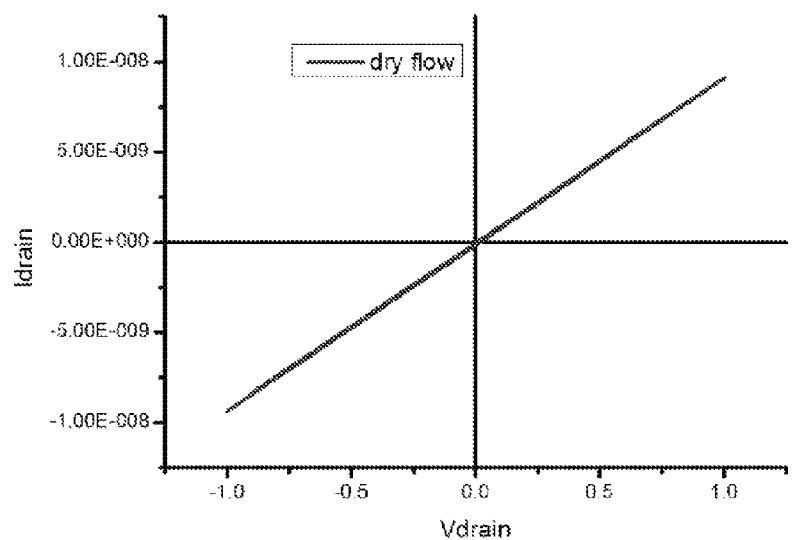
FIG. 9a shows the IV characteristics of a junction made from graphene oxide and reduced graphene oxide under dry air conditions.
Figure 9B:
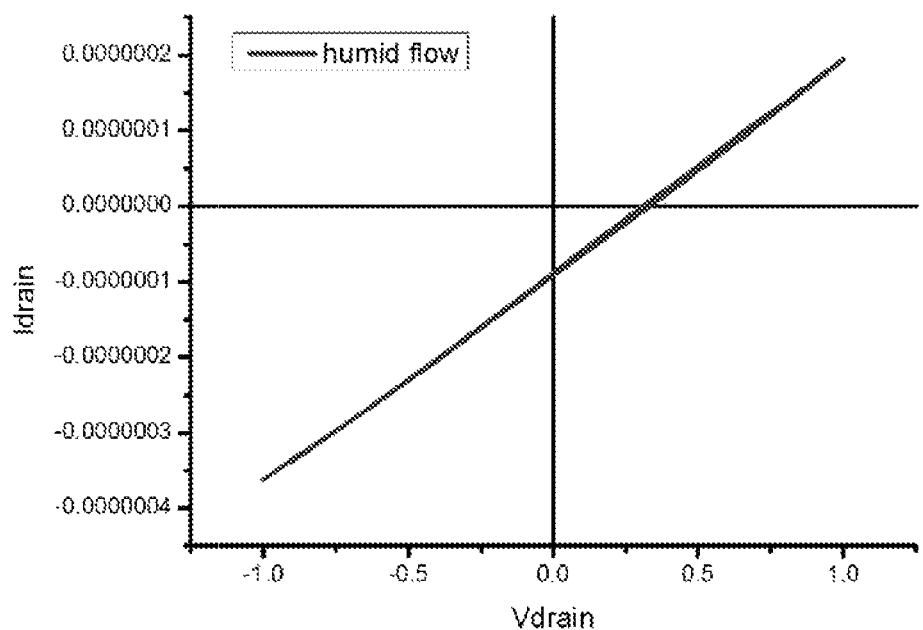
FIG. 9b shows the IV characteristics of a junction made from graphene oxide and reduced graphene oxide under humid air conditions.
Figure 9C:
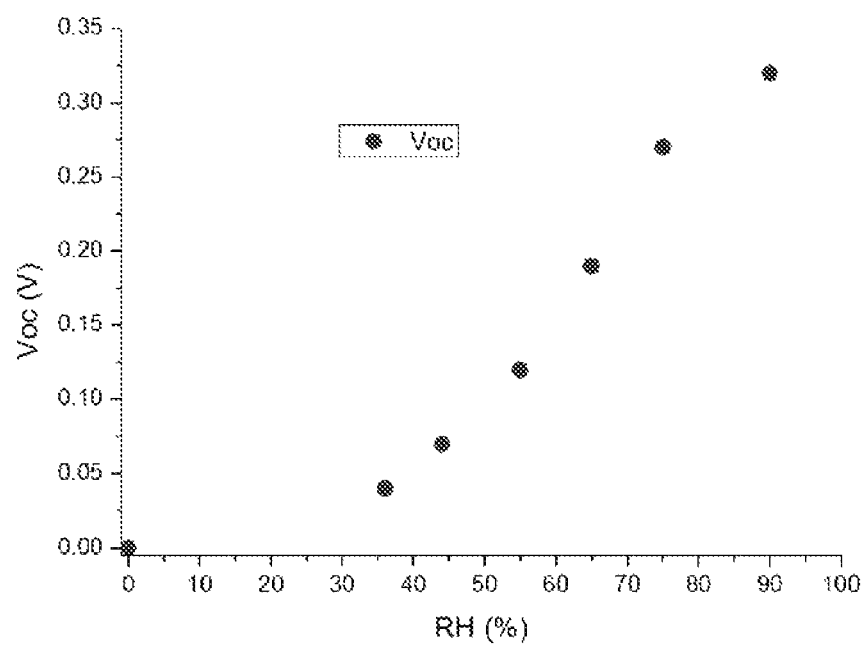
FIG. 9c shows the open circuit voltage of a junction made from graphene oxide and reduced graphene oxide as a function of humidity.

FIGS. 9a and 9b respectively show the IV characteristics of the graphene oxide junction in dry and humid air conditions, whilst FIG. 9c shows the open circuit voltage of the graphene oxide junction. As can be seen, this type of junction can provide an open circuit voltage ($V_{oc}$) ranging from 0V in dry air to over 0.3V in humid air.

Figure 10:
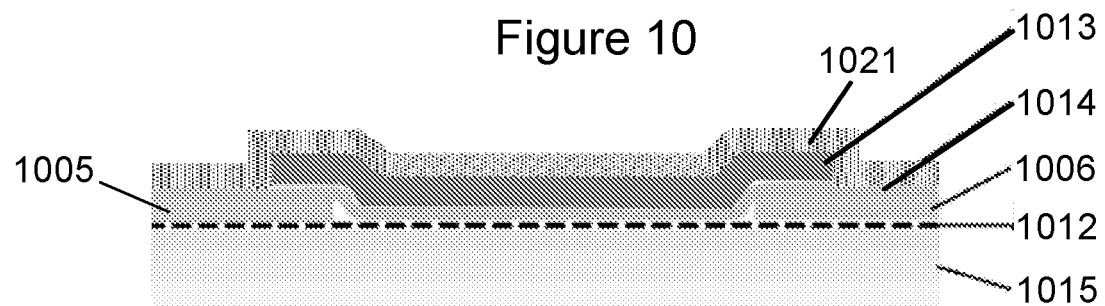
FIG. 10 shows an apparatus according to another embodiment of the present disclosure (cross-section)

FIG. 10 shows another embodiment of the present apparatus. In this example, the apparatus comprises a protective layer 1021 configured to prevent damage to the first 1012, second 1013 and third 1014 layers without preventing exposure of the second layer 1013 to the physical stimulus. When the apparatus is configured to detect/measure the humidity of the surrounding environment, for example, the protective layer 1021 may comprise a fluid-permeable material such as a block co-polymer or a non-absorbing fabric layer.

Figure 11:
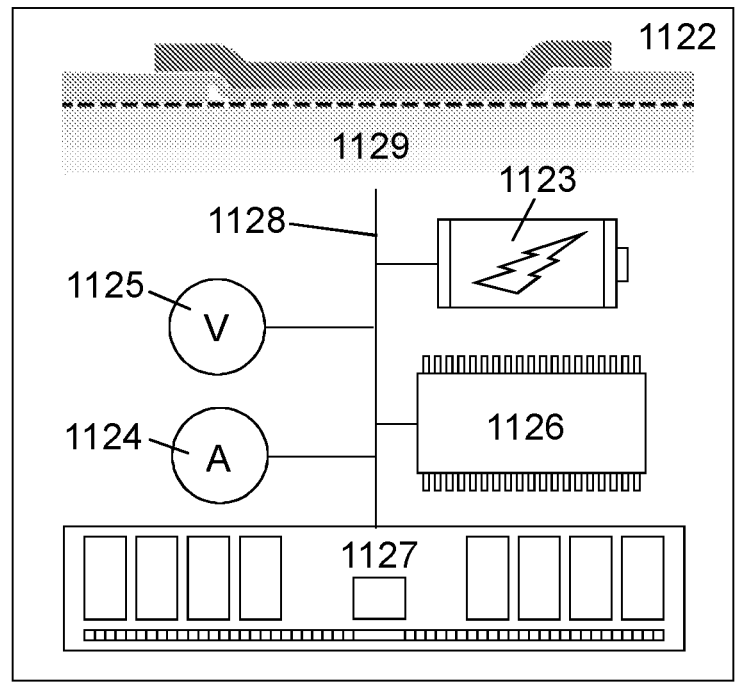
FIG. 11 shows an apparatus according to another embodiment of the present disclosure (schematic)

FIG. 11 shows a further embodiment of the apparatus described herein. The apparatus may be one or more of an electronic device, a portable electronic device, a portable telecommunications device, a sensor and a module for one or more of the same. In the example shown, the apparatus is a sensor 1122 comprising the first, second and third layers, source and drain electrodes (i.e. the components 1129 described previously), a power source 1123, an ammeter 1124, a voltmeter 1125, a processor 1126 and a storage medium 1127, which are electrically connected to one another by a data bus 1128.

The power source 1123 is configured to apply a voltage between the source and drain electrodes, the voltmeter 1125 is configured to measure the applied voltage, and the ammeter 1124 is configured to measure the resulting current flowing through the first layer.

The processor 1126 is configured for general operation of the apparatus 1122 by providing signaling to, and receiving signaling from, the other components to manage their operation. In addition, the processor 1126 is configured to receive the voltage and current measurements from the voltmeter 1125 and ammeter 1124, respectively, calculate the conductance (G=I/V) of the first layer, and derive the presence and/or magnitude of the physical stimulus using the calculated conductance. In another embodiment, the apparatus 1122 may comprise a conductance meter instead of (or in addition to) the voltmeter 1125 and ammeter 1124 in order to measure the conductance of the first layer directly, and the processor 1126 may be configured to receive the conductance measurement from the conductance meter and derive the presence and/or magnitude of the physical stimulus using the measured conductance.

The storage medium 1127 is configured to store computer code configured to perform, control or enable operation of the apparatus 1122. The storage medium 1127 may also be configured to store settings for the other components. The processor 1126 may access the storage medium 1127 to retrieve the component settings in order to manage the operation of the other components. The storage medium 1127 may also be configured to store calibration data (e.g. predetermined measurements of stimulus levels versus conductance) for use by the processor 1126 in deriving the presence and/or magnitude of the physical stimulus.

The processor 1126 may be a microprocessor, including an Application Specific Integrated Circuit (ASIC). The storage medium 1127 may be a temporary storage medium such as a volatile random access memory. On the other hand, the storage medium 1127 may be a permanent storage medium such as a hard disk drive, a flash memory, or a non-volatile random access memory.

Figure 12:
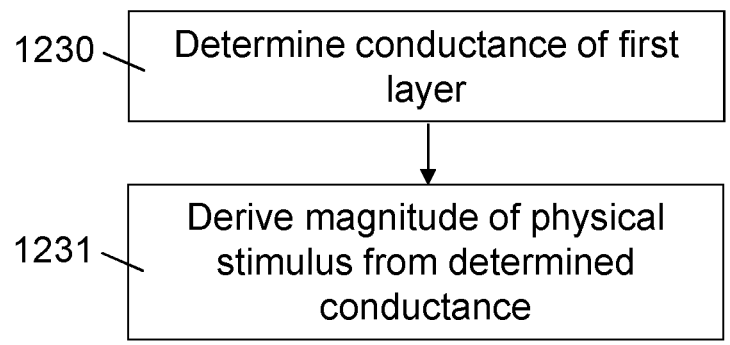
FIG. 12 shows the main steps of a method of using the apparatus described herein.

The main steps 1230-1231 of a method of using the apparatus to derive the presence and/or magnitude of the physical stimulus are shown schematically in FIG. 12. Similarly, the main steps 1332-1333 of a method of making the apparatus are shown schematically in FIG. 13.

A number of different fabrication processes may be used to form the above-mentioned apparatus. According to one example, a first layer material (e.g. graphene) is deposited on a supporting substrate (e.g. polyethylene terephthalate, polyethylene naphthalate, glass, silicon, silicon dioxide, polydimethylsiloxane or polyurethane). Electrical contacts are then formed on the first layer material (e.g. using inkjet, screen, stencil or flexographic printing; evaporation or sputtering) to produce the source and drain electrodes. Suitable electrode materials include metals such as gold, silver and copper; printed metals such as silver nanoparticles; multi-layer graphene; graphene ink or reduced graphene oxide. A conductive channel is then defined in the first layer using a subtractive process such as oxygen plasma etching or laser micromachining, before a third layer material (e.g. an ion gel or polymer electrolyte) is deposited thereon using drop casting or printing techniques. An ion gel may be formed by polymerising a block copolymer along with an ionic liquid so that self-assembled nanostructures are produced in which the ions are selectively soluble. A second layer material is then formed on top of the third layer material followed by an optional protective layer. When graphene oxide is used in the second layer, it may comprise a plurality of fully or partially oxidised graphene flakes with various functional groups attached thereto. Furthermore, the size and number of the oxidised graphene layers may vary. Graphene oxide solution (concentration: 1 g/L; composition: carbon (79%), oxygen (20%); flake size: 0.5-0.7 μm; and thickness: 1 atomic layer (at least 60%)) can be obtained from Graphene Square, Inc and deposited using spray coating, drop casting, spin coating or inkjet printing.

Figure 14:
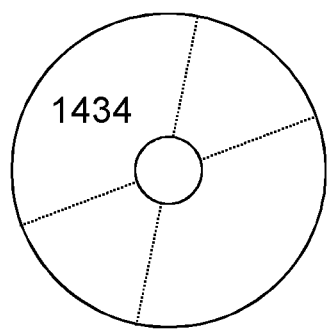
FIG. 14 shows a computer-readable medium comprising a computer program configured to perform, control or enable one or more of the method steps of FIG. 12 or 13.

FIG. 14 illustrates schematically a computer/processor readable medium 1434 providing a computer program according to one embodiment. In this example, the computer/processor readable medium 1434 is a disc such as a digital versatile disc (DVD) or a compact disc (CD). In other embodiments, the computer/processor readable medium 1434 may be any medium that has been programmed in such a way as to carry out an inventive function. The computer/processor readable medium 1434 may be a removable memory device such as a memory stick or memory card (SD, mini SD, micro SD or nano SD).

Figure 13:
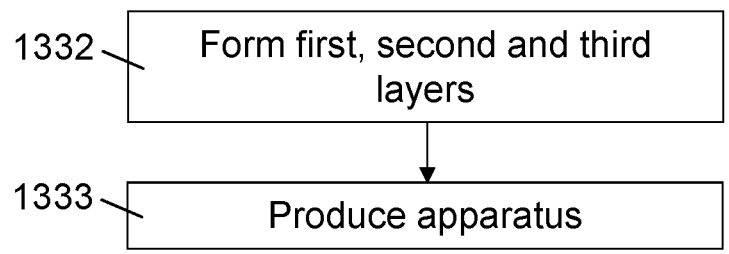
FIG. 13 shows the main steps of a method of making the apparatus described herein.

The computer program may comprise computer code configured to perform, control or enable one or more of the method steps 1230-1231, 1332-1333 of FIG. 12 or 13. In particular, the computer program may be configured to measure/calculate the conductance of the first layer, and derive the presence and/or magnitude of the physical stimulus using the measured/calculated conductance of the first layer. Additionally or alternatively, the computer program may be configured to control the above-mentioned fabrication processes to form the first, second and third layers of the apparatus.

Other embodiments depicted in the figures have been provided with reference numerals that correspond to similar features of earlier described embodiments. For example, feature number 1 can also correspond to numbers 101, 201, 301 etc. These numbered features may appear in the figures but may not have been directly referred to within the description of these particular embodiments. These have still been provided in the figures to aid understanding of the further embodiments, particularly in relation to the features of similar earlier described embodiments.

It will be appreciated to the skilled reader that any mentioned apparatus/device and/or other features of particular mentioned apparatus/device may be provided by apparatus arranged such that they become configured to carry out the desired operations only when enabled, e.g. switched on, or the like. In such cases, they may not necessarily have the appropriate software loaded into the active memory in the non-enabled (e.g. switched off state) and only load the appropriate software in the enabled (e.g. on state). The apparatus may comprise hardware circuitry and/or firmware. The apparatus may comprise software loaded onto memory. Such software/computer programs may be recorded on the same memory/processor/functional units and/or on one or more memories/processors/functional units.

In some embodiments, a particular mentioned apparatus/device may be pre-programmed with the appropriate software to carry out desired operations, and wherein the appropriate software can be enabled for use by a user downloading a "key", for example, to unlock/enable the software and its associated functionality. Advantages associated with such embodiments can include a reduced requirement to download data when further functionality is required for a device, and this can be useful in examples where a device is perceived to have sufficient capacity to store such pre-programmed software for functionality that may not be enabled by a user.

It will be appreciated that any mentioned apparatus/circuitry/elements/processor may have other functions in addition to the mentioned functions, and that these functions may be performed by the same apparatus/circuitry/elements/processor. One or more disclosed aspects may encompass the electronic distribution of associated computer programs and computer programs (which may be source/transport encoded) recorded on an appropriate carrier (e.g. memory, signal).

It will be appreciated that any "computer" described herein can comprise a collection of one or more individual processors/processing elements that may or may not be located on the same circuit board, or the same region/position of a circuit board or even the same device. In some embodiments one or more of any mentioned processors may be distributed over a plurality of devices. The same or different processor/processing elements may perform one or more functions described herein.

It will be appreciated that the term "signaling" may refer to one or more signals transmitted as a series of transmitted and/or received signals. The series of signals may comprise one, two, three, four or even more individual signal components or distinct signals to make up said signaling. Some or all of these individual signals may be transmitted/received simultaneously, in sequence, and/or such that they temporally overlap one another.

With reference to any discussion of any mentioned computer and/or processor and memory (e.g. including ROM, CD-ROM etc), these may comprise a computer processor, Application Specific Integrated Circuit (ASIC), field-programmable gate array (FPGA), and/or other hardware components that have been programmed in such a way to carry out the inventive function.

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed aspects/embodiments may consist of any such individual feature or combination of features. In view of the foregoing description it will be evident to a person skilled in the art that various modifications may be made within the scope of the disclosure.

While there have been shown and described and pointed out fundamental novel features as applied to different embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment may be incorporated in any other disclosed or described or suggested form or embodiment as a general matter of design choice. Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An apparatus comprising:
a first layer configured to enable a flow of charge carriers from a source electrode to a drain electrode;
a second layer configured to generate a voltage in response to a physical stimulus which is proportional to the magnitude of the physical stimulus, the second layer positioned such that the generated voltage can affect a conductance of the first layer; and
a third layer positioned between the first and second layers to prevent a flow of charge carriers therebetween,
wherein the third layer comprises a material configured to form electric double-layers at the interfaces with the first and second layers in response to the generated voltage, formation of the electric double-layers enhancing an effect of the generated voltage on the conductance of the first layer such that determination of the conductance of the first layer can be used to allow a presence, magnitude, or any combination thereof of the physical stimulus to be derived, wherein the physical stimulus comprises a chemical or biological species, and the second layer is configured to generate a voltage which is proportional to an amount of chemical or biological species to which the second layer is exposed, and wherein the chemical or biological species is water, and the second layer comprises a junction of graphene oxide and reduced graphene oxide.

2. The apparatus of claim 1, wherein the second layer comprises a junction of first and second materials each having one or more functional groups configured to release charged particles on interaction with the chemical or biological species, and wherein the first material has a higher concentration of charge-releasing functional groups than the second material such that a concentration gradient of charged particles is produced at the junction on exposure to the chemical or biological species to generate the voltage.

3. The apparatus of claim 1, wherein the physical stimulus comprises heat, and the second layer comprises a pyroelectric material configured to generate a voltage which is proportional to the temperature of the pyroelectric material.

4. The apparatus of claim 1, wherein the physical stimulus comprises electromagnetic radiation, and the second layer comprises a photovoltaic cell configured to generate a voltage which is proportional to the intensity of electromagnetic radiation incident upon the photovoltaic cell.

5. The apparatus of claim 1, wherein the physical stimulus comprises mechanical stress, and the second layer comprises a piezoelectric material configured to generate a voltage which is proportional to the magnitude of stress applied to the piezoelectric material.

6. The apparatus of claim 1, wherein the physical stimulus comprises an electric field, and the second layer comprises a ferroelectric material configured to generate a voltage which is proportional to a strength of electric field to which the ferroelectric material is exposed.

7. The apparatus of claim 1, wherein the apparatus has a substantially planar configuration in which the second layer is adjacent to the first layer, or has a stacked configuration in which the second layer overlies the first layer.

8. The apparatus of claim 1, wherein the first layer has a thickness of one atomic layer.

9. The apparatus of claim 1, wherein the first layer is patterned to form a channel between the source and drain electrodes.

10. The apparatus of claim 1, wherein the material of the third layer comprises one or more of a liquid and a gel.

11. The apparatus of claim 1, wherein the apparatus comprises a gate electrode positioned between the second and third layers.

12. The apparatus of claim 1, wherein the apparatus comprises a protective layer configured to prevent damage to at least the second layer without preventing exposure of the second layer to the physical stimulus.

13. The apparatus of claim 1, wherein the apparatus comprises the source and drain electrodes.

14. The apparatus of claim 1, wherein the physical stimulus comprises water, and wherein determination of the conductance of the first layer can be used to provide an indication of a relative humidity of an environment in which the apparatus is located.

15. The apparatus of claim 1, wherein the apparatus comprises means for determining the conductance of the first layer, and means for deriving the magnitude of the physical stimulus using a determination of the conductance of the first layer.

16. The apparatus of claim 1, wherein the apparatus is one or more of an electronic device, a portable electronic device, a portable telecommunications device, a sensor and a module for any of the aforementioned devices.

17. A method, comprising:
enabling a flow of charge carriers in a first layer from a source electrode to a drain electrode;
generating voltage in a second layer in response to a physical stimulus which is proportional to a magnitude of the physical stimulus, the second layer positioned such that the generated voltage can affect a conductance of the first layer; and
preventing a flow of charge carriers in a third layer positioned between the first and second layers,
wherein the third layer comprises a material configured to form electric double-layers at the interfaces with the first and second layers in response to the generated voltage, formation of the electric double-layers enhancing an effect of the generated voltage on the conductance of the first layer such that determination of the conductance of the first layer can be used to allow a presence, magnitude, or any combination thereof of the physical stimulus to be derived, wherein the physical stimulus comprises a chemical or biological species, and the second layer is configured to generate a voltage which is proportional to an amount of chemical or biological species to which the second layer is exposed, and wherein the chemical or biological species is water, and the second layer comprises a junction of graphene oxide and reduced graphene oxide;
determining the conductance of the first layer; and
deriving the presence and/or magnitude of the physical stimulus using the determined conductance of the first layer.

18. A non-transitory computer readable medium comprising code that, when executed by a processing device, cause the processing device to perform:
enabling a flow of charge carriers in a first layer from a source electrode to a drain electrode;
generating voltage in a second layer in response to a physical stimulus which is proportional to a magnitude of the physical stimulus, the second layer positioned such that the generated voltage can affect a conductance of the first layer; and
preventing a flow of charge carriers in a third layer positioned between the first and second layers,
wherein the third layer comprises a material configured to form electric double-layers at the interfaces with the first and second layers in response to the generated voltage, formation of the electric double-layers enhancing an effect of the generated voltage on the conductance of the first layer such that determination of the conductance of the first layer can be used to allow a presence, magnitude, or any combination thereof of the physical stimulus to be derived, wherein the physical stimulus comprises a chemical or biological species, and the second layer is configured to generate a voltage which is proportional to an amount of chemical or biological species to which the second layer is exposed, and wherein the chemical or biological species is water, and the second layer comprises a junction of graphene oxide and reduced graphene oxide;
determining the conductance of the first layer; and
deriving the presence and/or magnitude of the physical stimulus using the determined conductance of the first layer.

19. The method of claim 17, wherein:
the second layer comprises a junction of first and second materials each having one or more functional groups configured to release charged particles on interaction with the chemical or biological species, and
the first material has a higher concentration of charge-releasing functional groups than the second material such that a concentration gradient of charged particles is produced at the junction on exposure to the chemical or biological species to generate the voltage.

20. The method of claim 17, wherein the generated voltage in the second layer in response to a physical stimulus is distributed via operation of a gate electrode positioned between the second and third layers.

* * * * *